United States Patent [19]

Genaro

[11] Patent Number: 4,923,440

[45] Date of Patent: May 8, 1990

[54] DEVICE FOR CONTAINMENT AND INSERTION OF TAMPONS AND OTHER OBJECTS

[75] Inventor: Donald M. Genaro, Haworth, N.J.

[73] Assignee: Henry Dreyfuss Associates, New York, N.Y.

[21] Appl. No.: 216,119

[22] Filed: Jul. 7, 1988

Related U.S. Application Data

[63] Continuation-in-part of Ser. No. 102,611, Sep. 30, 1987.

[51] Int. Cl.⁵ .............................................. A61F 13/20
[52] U.S. Cl. ........................................ 604/14; 604/11
[58] Field of Search ................................ 604/11–18, 604/904, 285–288

[56] References Cited

U.S. PATENT DOCUMENTS

| 2,268,536 | 12/1941 | Seidler | 609/11 |
| 2,355,917 | 8/1944 | Knight | 604/11 |
| 2,509,241 | 5/1950 | Mende | 604/11 |
| 3,358,686 | 12/1967 | Asaka | 604/14 |
| 3,857,394 | 12/1974 | Alemany | 604/14 |
| 4,127,339 | 11/1978 | Malacheski et al. | 401/132 |
| 4,286,594 | 9/1981 | Cunningham | 128/263 |
| 4,318,404 | 3/1982 | Cunningham | 128/263 |
| 4,648,867 | 3/1987 | Conder et al. | 604/14 |

FOREIGN PATENT DOCUMENTS

| 0104039 | 3/1984 | European Pat. Off. | 604/14 |
| 0614378 | 11/1979 | Sweden | 604/288 |

Primary Examiner—C. Fred Rosenbaum
Assistant Examiner—Mark O. Polatta
Attorney, Agent, or Firm—Fitzpatrick, Cella, Harper & Scinto

[57] ABSTRACT

An improved device for containing and inserting tampons, suppositories and other objects includes the suppository or object, a transporter comprising a sheath or a combination of straps which surrounds the suppository or object and is open at one end, a long hollow cylinder, a short hollow cylinder attached to said transporter and slidably mounted on the outside of the long cylinder. The elements are arranged such that the tampon or other object may be inserted into an opening without frictional movement between the opening and either the long hollow cylinder or the sheath or the straps. The device is significantly more compact than prior art applicator devices and provides for smoothness and ease of insertion.

17 Claims, 3 Drawing Sheets

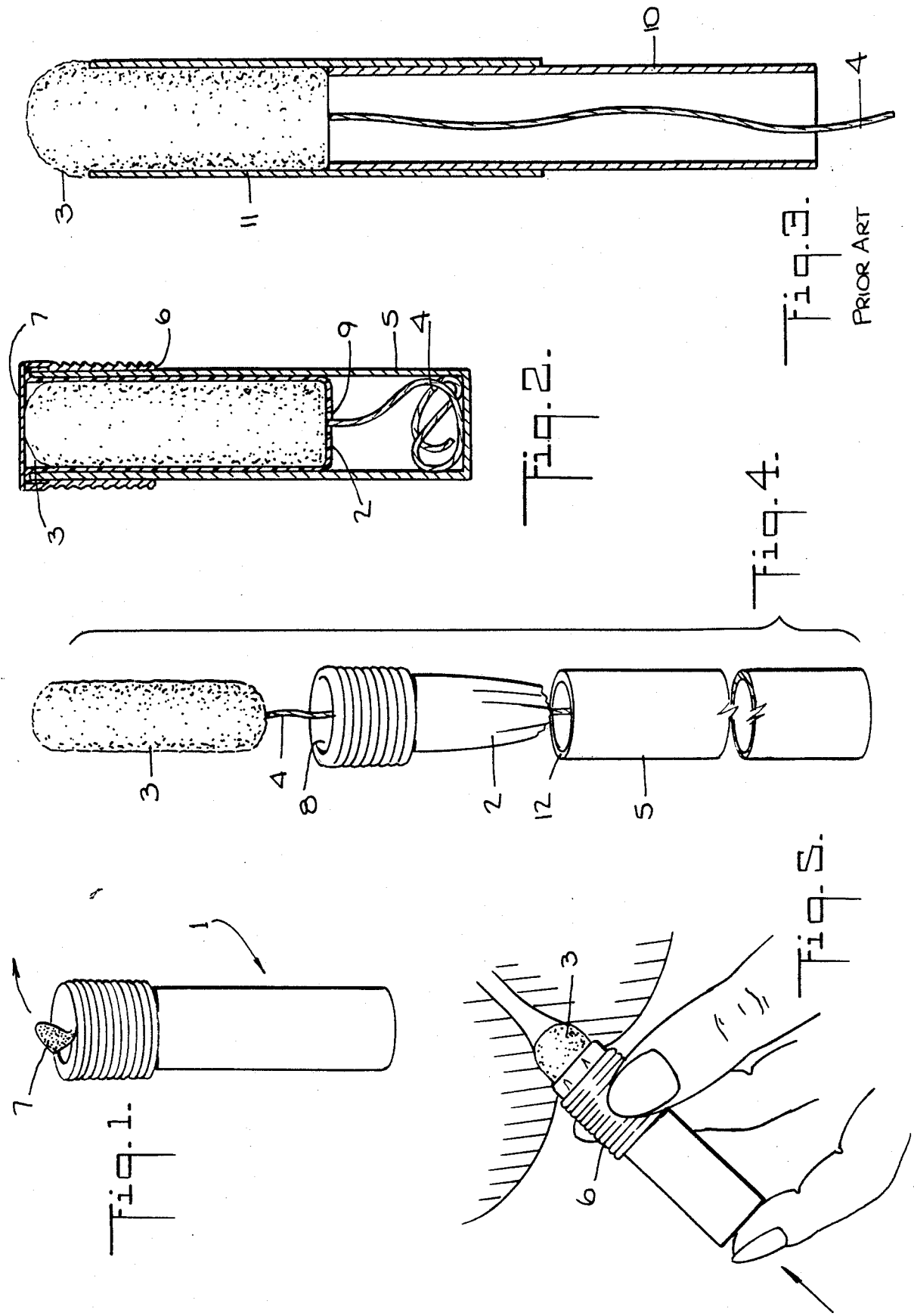

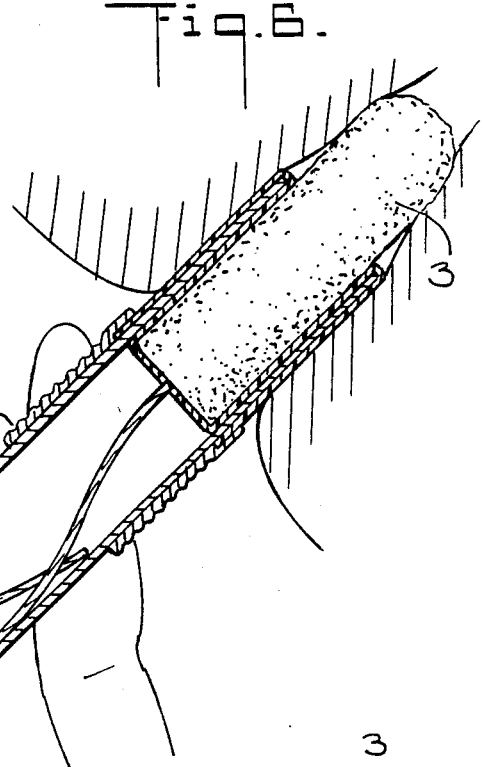
Fig.6.
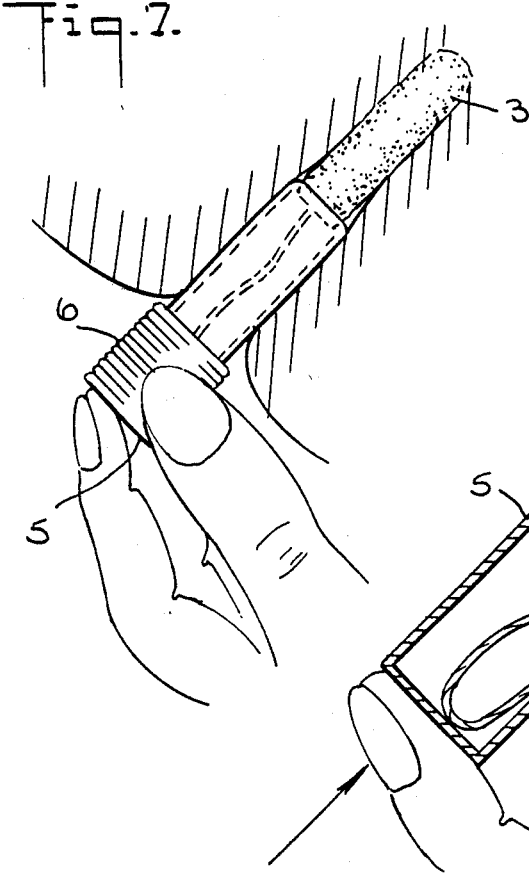
Fig.7.
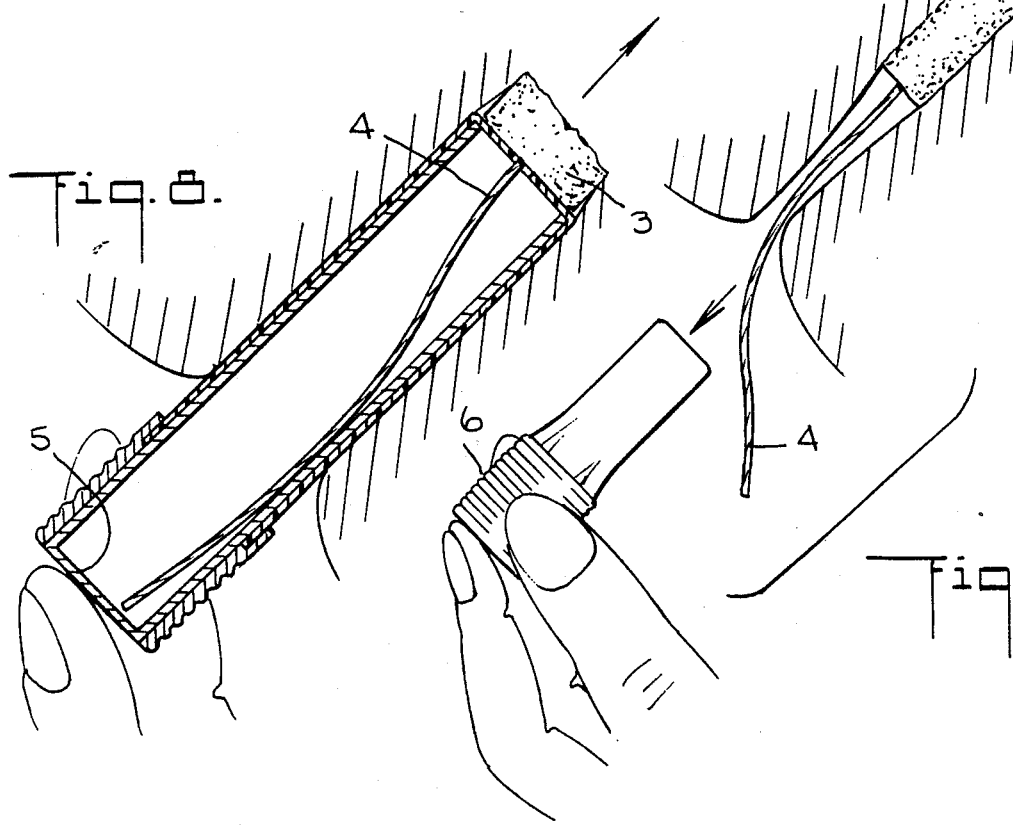
Fig.8.
Fig.9.

DEVICE FOR CONTAINMENT AND INSERTION OF TAMPONS AND OTHER OBJECTS

This is a continuation-in-part of U.S. Pat. Application Ser. No. 102,611, filed Sept. 30, 1987.

BACKGROUND OF THE INVENTION

1. Field of the Invention

This invention relates to the containment and administration of tampons, suppositories and other objects to be inserted into openings. More specifically, the disclosed device is particularly suitable for sterile containment and sterile insertion of a variety of objects, such as medication, suppositories or tampons, into body openings. In general, the device comprises (i) a package for compact, sanitary storage of an object to be inserted and (ii) an insertion device comprising a combination of a transporter, a long hollow cylinder and a short hollow cylinder.

2. Description of the Prior Art

Devices for the insertion of objects are well known and widely used. For example, with respect to tampons, one widely accepted method of insertion is by use of two concentric hollow tubes, although tampons may also be inserted by direct placement using one's hand. Insertion devices generally include an outer tube, a tampon positioned therein, and a pusher tube, which is placed behind the tampon and within the outer tube. These insertion devices are themselves placed into the body opening and withdrawn subsequent to the insertion of the object.

Insertion by direct placement without an insertion device has the disadvantage of possibly contaminating the opening and soiling one's hand as a result of contact between the hand and the body or bodily opening. While insertion devices may reduce the likelihood or degree of such contact, they cause friction upon insertion and constitute a foreign object which must be kept sanitary and as smooth as possible.

The present invention is particularly suitable for containment and insertion of tampons and medical suppositories. In a preferred form, the device provides a sterile receptacle for storage of the object, as well as a device for sterile insertion of the object. Typically, the object to be inserted will be a suppository or a tampon, but a wide variety of objects, such as medications or supply cartridges for machinery, are also contemplated. The object need not be solid but may under the proper conditions be pellets, granules, gelatin, or even a liquid. Moreover, while the device may be used to insert objects into openings in the body, the device may also be used in connection with many openings, such as the breech in a dispenser unit or the fuel port for medical irradiation devices.

SUMMARY OF THE INVENTION

The device of this invention permits insertion with little or no relative movement between the insertion device and the opening. This invention can also provide a compact, sanitary insertion device with smooth surfaces for ease of insertion.

As contemplated, the present invention comprises three elements in a single assembly: a protective package, an object to be inserted, and an insertion device. More specifically, the invention comprises (a) a smooth, flexible transporter or carrier which at least partially surrounds the object and is open at least at one end; (b) a long hollow cylinder which contains the object and the transporter; and (c) a short hollow cylinder which has a surface area suitable for grasping by the fingers (including optionally the thumb) for the application of axial force to the short cylinder. The short hollow cylinder has the open end of the transporter affixed concentrically to it and is slidably mounted on the outside of the long cylinder. The elements are arranged such that as the short cylinder is moved axially relative to the long cylinder by application of axial force to one end of the long cylinder and application of axial force in the opposite direction to the short cylinder by one or more fingers grasping the outside of the short cylinder, the transporter is drawn over one end of the long cylinder. The transporter thus propels the object out of the long cylinder.

If the transporter is a sheath that completely surrounds the sides of the object, the transporter covers and provides a smooth surface to the leading edge of the long cylinder. If such a device is placed proximate to an opening, such as a body opening, and the long cylinder is used to guide and insert the object into the body, the sheath provides a soft cover for the leading edge of the long cylinder.

In the present invention, the transporter is moved into contact with the interior of the opening in such a way that there is a minimum of relative movement between the transporter and the interior of the opening. In fact, it is possible with careful handling to reduce to zero the movement of the transporter relative to the interior surface of the opening.

The length of the short cylinder and the length of the long cylinder may be adjusted and adapted for the particular desired use. The short cylinder will usually be long enough to permit easy grasping by the fingers. The length of long cylinder will usually be enough to reach into the opening as far as the desired final location of the tampon or other object to be inserted. The difference in the lengths of the two cylinders is preferably approximately the distance for insertion to final location of the object in the opening.

For storage before insertion the device may include a removable cover at the open end of a transporter sheath to provide additional protection to the object to be inserted. With proper selection of materials it is possible with this invention to keep the object sanitary. As other additional and optional features, the object may have a string for removal after insertion and the transporter may have a small hole in it to guide and locate the string after insertion. Also, the long hollow cylinder may be closed at one end to provide for cleanliness and/or to carry the removal string.

The device of this invention provides several advantages over the prior art. It is significantly more compact than prior art insertion devices. By its possible combination of sheath and closure, this invention may provide a small but completely sanitary package. For example, such devices of this invention may be carried loose in a medical kit or a handbag without danger of contaminating the object to be inserted or the surfaces of the insertion device that will contact the body opening. The system also permits sanitary, one-handed direct insertion of the object. The use of this invention reduces or eliminates contact between hand and body.

In addition, the invention has several features which provide for smooth and easy insertion. With the present invention there is little or no relative movement between either the transporter or the long cylinder and the interior of the body.

The use of the sheath embodiment permits complete insertion without the rigid and often rough insertion device (long cylinder, sometimes referred to in the art as an "applicator") ever coming into contact with the body. Moreover, the leading edge of the long cylinder is covered by the soft sheath. After insertion, the sheath and cylinders are removed, and if a removal string was used and led through a small hole in the closed end of the sheath, the string is placed in proper position for later use.

As a further improvement over certain prior art applicators that require plastic shapes to provide for ease and smoothness of insertion, the present applicator cylinders and transporter provide ease and smoothness of insertion but may be made entirely from bio-degradable materials.

BRIEF DESCRIPTION OF THE DRAWINGS

FIG. 1 is a perspective of a device constructed in accordance with the present invention.

FIG. 2 is a cross-section of FIG. 1.

FIG. 3 is a cross-section of a prior art device, showing in comparison with FIG. 2 the compact nature of the present invention.

FIG. 4 is a perspective of the device of FIG. 1 partially disassembled and exploded.

FIGS. 5 to 9 are in partial perspective and partial cross-section and show use of the device of FIG. 1.

DESCRIPTION OF THE PREFERRED EMBODIMENT

Figure 10:
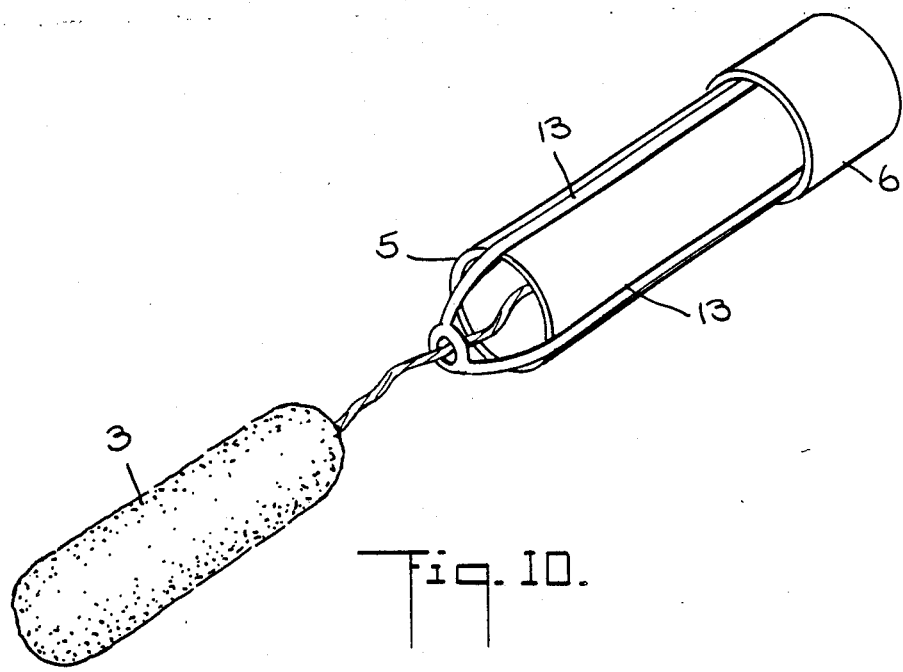
FIG. 10 is a perspective of an alternative device of the present invention, partially disassembled and exploded.

The invention will be described with specific reference to a system for containing, storing, and transporting tampons. However, as described above in the Summary of the Invention, the invention is adaptable to the insertion of a wide variety of objects into different types of openings, and therefore should not be limited to the particular embodiment disclosed herein.

Referring now specifically to the drawings, reference numeral 1 identifies a suppository device of the present invention, which includes a protective sheath 2 (semi-transparent in these drawings but which may preferably be opaque), a tampon 3, a withdrawal string 4, a long hollow cylinder 5, a short hollow cylinder 6, and a removable closure 7. The sheath is open at one end 8 and, as shown in FIG. 2, the withdrawal string 4 may pass through a second opening 9.

FIG. 3 shows a prior art applicator type device for inserting a tampon 3, with its long pusher cylinder 10 and its long holding cylinder 11. As shown by comparison with FIG. 2, the applicator device of the present invention is significantly more compact, in addition to providing the advantages of ease of insertion already referred to.

FIG. 1 shows the removal of a closure 7 by peeling it off of the open end 8 of the sheath 2. As shown in FIGS. 5, 6, 7 and 8, during insertion the soft, smooth sheath covers the leading edge of the rigid hollow cylinder 5. The use of an applicator reduces or eliminates contact between the body opening and the hand.

Also as shown in FIGS. 5, 6, 7 and 8, as the short cylinder 6 is moved axially relative to the long cylinder by grasping the short cylinder with the fingers and pushing on one end of the long cylinder with one or more other fingers, the sheath is drawn over the leading edge 12 of the long cylinder 5. This in turn propels or transports the object 3 out of the long cylinder 5 and out of the sheath 2 into the body opening. At the same time, the sheath, as it is everted by the movement of the two cylinders, is moved into contact with the interior of the opening, but there is little or no relative movement between the sheath and the interior surface of the body opening during insertion. In FIG. 9, the tampon is fully inserted, and the withdrawal string 4 is now in its proper location.

As is apparent, only the smooth surface of the sheath contacts the body. Moreover, the surface of the sheath that contacts the body was originally the interior, protected, sanitary surface of the sheath. In addition, the fingers and hand need make no contact with the body orifice.

If object 3 is a tampon such as a catememial receptor is to be inserted, it may be made of any absorbing material appropriate for the purpose. If object 3 is a suppository and the device is to be used for insertion of the suppository, the suppository may be any of various well-known medicated suppositories having a cylindrical or conical shape, although the invention is not limited to the insertion of objects having only these shapes. The closure may be made of paper, foil, or other similar material, and is removably secured to the sheath by use of a peelable adhesive or other securing means. If the closure is made of a properly selected material, such as a foil, the package can be made tamper-proof. The sheath may be made of latex, treated paper or other synthetic or natural flexible, thin material. The cylinders may be made of cardboard or other thin, rigid or semi-rigid material, with the sheath adhered by adhesive onto the end of the short cylinder or held between two laminated pieces which may be used to make up the short cylinder.

An advantage of the present invention is that smoothness may be attained comparable to that previously attainable only with plastic tipped applicators which are not bio-degradable. All parts of the device are preferably bio-degradable.

Exemplary dimensions of the system for the device are an overall diameter of about three-quarters of an inch, with the interior of the long cylinder being about one-half of an inch in diameter, a tampon length of about two inches, and a sheath of about 2½ inches in length and five-eighths of an inch in diameter.

Figure 11:
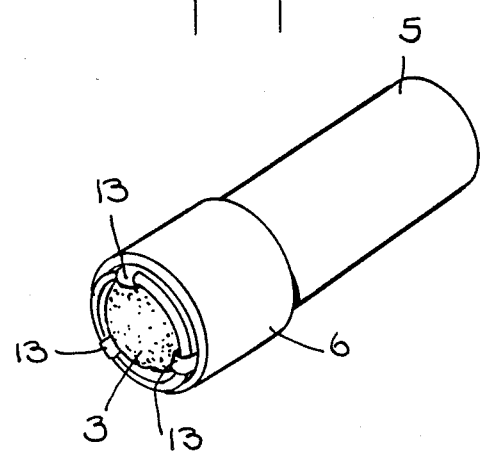
FIG. 11 is a perspective of the device of FIG. 10 in assembled form.

The alternative device shown in FIGS. 10 and 11 comprise one or more transporter straps 13, and preferably three such straps. These straps are affixed at one end to the short cylinder 6. At their other end they are affixed to each other at 14, which may have a second opening 9 for managing the withdrawal string. The straps are preferably made of thin bio-degradeable film and possess limited stretch and low friction properties. They are also preferably very flexible. (Their curved position near the portion 14 in FIG. 10 is not because they are necessarily stiff and assume that shape naturally. Their curved position in FIG. 10 is a consequence of showing clearly their relationship to other parts of the invention in a partially disassembled and exploded view.)

In the initial position, as shown in FIG. 11, the transporter straps 13 hold the tampon 3 or other object to be inserted at least partially inside the long cylinder 5. As the short cylinder 6 is moved along the long cylinder 5, the straps 13 hold and propel or transport the object 3 from the long cylinder 5 into the opening which is intended to receive the object 3. The withdrawal string 4 in this embodiment may pass through the hole 9 in the straps near point 14, as shown in FIG. 10. Alternatively, the string 4 may pass between two straps 13 and beside the point 14.

The principal advantage of the transporter straps of the device of FIGS. 10 and 11 is reduced friction relative to the use of the transporter sheath in the device of FIGS. 1 and 2. The straps, as they bear against and travel over the end of long cylinder 5, create less frictional resistance to movement than the sheath 2 does in traveling over the end of long cylinder 5 in the device of FIGS. 1 and 2. The reduced sanitary protection of the FIG. 10 device relative to the device of FIG. 2 can be compensated for by packaging the entire device in a sanitary wrapper. This is particularly easy and economical because of the compact nature of the present invention.

The foregoing is considered illustrative of the principles of the invention. Variations and modifications will be recognized, and it is hence not desired or intended to limit the invention to the exact construction and procedures described. Rather, all appropriate modifications and equivalents may be used.

We claim:

1. A containment and insertion device comprising:
   an object to be inserted into an opening;
   a flexible transporter that is separate from and unattached to the object and which at least partially surrounds the object and which is open at least at one end;
   an inner container which contains the object and the transporter;
   an outer container having a grasping surface means extending longitudinally along the outer container, an axial force being applicable by fingers grasping the grasping surface means, the outer container being slidably mounted on the outside of said inner container and being affixed to the open end of the transporter;
   the object, transporter, and containers being arranged such that fingers grasping the grasping surface means of the outer container apply an axial force to the outer container, and as the inner container is moved axially relative to the outer container (a) the transporter is drawn over one end of the inner contain (b) the object is propelled by the transporter out of the inner container and (c) the transporter and the containers may be withdrawn without withdrawal of the object.

2. The device of claim 1, wherein said object comprises a catememial receptor.

3. The device of claim 1, wherein said object comprises a suppository.

4. The device of claim 1, wherein said object comprises a tampon.

5. The device of claim 1 in which the transporter is a smooth sheath arranged such that the inner container does not contact said opening and the sheath provides a smooth cover for the end of the inner container.

6. The device of claim 5 which comprises in addition a peelable closure covering the open end of the sheath.

7. The device of claim 6 in which the sheath, the containers and the closure in combination constitute a sanitary package for the object.

8. A containment and insertion device comprising:
   an object to be inserted into an opening;
   a flexible transporter comprising one or more straps, wherein said transporter is separate from the object, at least partially surrounds the object, and is open at least at one end;
   an inner container which contains the object and the transporter;
   an outer container (i) having a surface area suitable for grasping by fingers for applying axial force, (ii) being slidably mounted on the outside of said hollow inner container and (iii) being affixed to the open end of the transporter;
   the object, transporter, and containers being arranged such that as the outer portion is moved axially relative to the inner container (a) the transporter is drawn over one end of the inner container and (b) the object is propelled by the transporter out of the inner container.

9. The device of claim 8, wherein said object comprises a catamenial receptor.

10. The device of claim 8, wherein said object comprises a suppository.

11. The device of claim 8, wherein said object comprises a tampon.

12. The device of claim 8, which comprises in addition a package for holding said device.

13. The system of claim 12 in which the transporter, the containers and the package in combination constitute a sanitary package for the object.

14. The device of claim 8, wherein the outer container is shorter than the inner container, and wherein the difference in the length of the containers is a predetermined length that corresponds to an insertion depth within the opening.

15. The device of claim 1, wherein the outer container is shorter than the inner container, and wherein the difference in the length of the containers is a predetermined length that corresponds to an insertion depth within the opening.

16. A method of inserting an object comprising the steps of:
   placing the object within a transporter which is capable of at least partially surrounding the object and is open at least at one end;
   placing the object and the transporter substantially inside an inner container;
   affixing the open end of the transporter to an outer container which is slidably mounted on the outside of the inner container;
   placing the object proximate to an opening;
   inserting the object into the opening by applying axial force to one end of the inner container and applying axial force in the opposite direction to the outer container while substantially eliminating axial forces on the opening; and
   withdrawing the transporter and the container from the opening.

17. The process of claim 16 including the step of removing a closure that provides additional protection to the object.

* * * * *